US007960149B2

(12) United States Patent
Harris et al.

(10) Patent No.: US 7,960,149 B2
(45) Date of Patent: Jun. 14, 2011

(54) POLYPEPTIDES HAVING BETA-GLUCOSIDASE ACTIVITY AND POLYNUCLEOTIDES ENCODING SAME

(75) Inventors: Paul Harris, Carnation, WA (US); Elizabeth Golightly, Reno, NV (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 12/707,154

(22) Filed: Feb. 17, 2010

(65) Prior Publication Data

US 2010/0196968 A1 Aug. 5, 2010

Related U.S. Application Data

(62) Division of application No. 11/760,243, filed on Jun. 8, 2007, now Pat. No. 7,670,819, which is a division of application No. 10/976,660, filed on Oct. 28, 2004, now Pat. No. 7,244,605.

(60) Provisional application No. 60/515,482, filed on Oct. 28, 2003.

(51) Int. Cl.
*C12P 19/02* (2006.01)
*C12N 9/00* (2006.01)
*C12N 9/26* (2006.01)
*C12N 1/20* (2006.01)
*C12N 15/00* (2006.01)

(52) U.S. Cl. ..... 435/105; 435/183; 435/201; 435/252.3; 435/320.1; 536/23.2

(58) Field of Classification Search ......... None
See application file for complete search history.

(56) References Cited

U.S. PATENT DOCUMENTS 6,087,131 A 7/2000 Gunata et al.

FOREIGN PATENT DOCUMENTS

| WO | WO 01/36586 | 5/2001 |
| WO | WO 02/095014 | 11/2002 |
| WO | WO 03/012071 | 2/2003 |
| WO | WO 2004/099228 | 11/2004 |
| WO | WO 2005/030926 | 4/2005 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Ximenes et al., 1996, *Current Microbiology* 32: 119-123.
Hang and Woodams, 1994, *Lebensmittel-Wissenschaft and Technologie* 27: 587-589.
Kitpreechavanich et al., *Agricultural and Biological Chemistry* 50: 1703-1712, (1986).
Kawaguchi et al., "Cloning and sequencing of the cDNA encoding beta-glucosidase 1 from *Aspergillus aculeatus*", Gene, vol. 173, No. 2, Sep. 16, 1996, p. 287-288.
Fontaine et al., "Differential patterns of activity displayed by two exo-beta-1, 3-gluconases associated with the *Aspergillus fumigatus* cell wall", Journal of Bacteriology, vol. 179, No. 10, 1997, p. 3154-3163.
Woodward et al., "Fungal and other Beta-D-Glucosidases—Their properties and applications", Enzyme and Microbial Technology, Stoneham MA, US, vol. 4, Mar. 1982, p. 73-79.

* cited by examiner

*Primary Examiner* — Christian Fronda
(74) *Attorney, Agent, or Firm* — Robert L. Starnes

(57) ABSTRACT

The present invention relates to isolated polypeptides having beta-glucosidase activity and isolated polynucleotides encoding the polypeptides. The invention also relates to nucleic acid constructs, vectors, and host cells comprising the polynucleotides as well as methods for producing and using the polypeptides.

9 Claims, 13 Drawing Sheets

```
ATGAGATTCGGTTGGCTCGAGGTGGCCGCTCTGACGGCCGCTTCTGTAGCCAATGCCCAGGTTTGTGATGCTTTCCCGTCATTGTTTCGGATATAGTTGA 100
 M  R  F  G  W  L  E  V  A  A  L  T  A  A  S  V  A  N  A  Q
CAATAGTCATGGAAATAATCAGGAATTGGCTTTCTCTCCACCATTCTACCCTTCGCCTTGGGCTGATGGCCAGGGAGAGTGGGCAGATGCCCATCGACGC 200
                E  L  A  F  S  P  P  F  Y  P  S  P  W  A  D  G  Q  G  E  W  A  D  A  H  R  R
GCCGTCGAGATCGTTTCTCAGATGACACTGGCGGAGAAGGTTAACCTTACAACGGGTACTGGGTGGGTTGCGACTTTTTTGTTGACAGTGAGCTTTCTTC 300
 A  V  E  I  V  S  Q  M  T  L  A  E  K  V  N  L  T  T  G  T  G
ACTGACCATCTACACAGATGGGAAATGGACCGATGCGTCGGTCAAACCGGCAGCGTTCCCAGGTAAGCTTGCAATTCTGCAACAACGTGCAAGTGTAGTT 400
               W  E  M  D  R  C  V  G  Q  T  G  S  V  P  R
GCTAAAACGCGGTGGTGCAGACTTGGTATCAACTGGGGTCTTTGTGGCCAGGATTCCCCTTTGGGTATCCGTTTCTGTGAGCTATACCCGCGGAGTCTTT 500
                L  G  I  N  W  G  L  C  G  Q  D  S  P  L  G  I  R  F
CAGTCCTTGTATTATGTGCTGATGATTGTCTCTGTATAGCTGACCTCAACTCCGCCTTCCCTGCTGGTACTAATGTCGCCGCACATGGGACAAGACACT 600
                          S  D  L  N  S  A  F  P  A  G  T  N  V  A  A  T  W  D  K  T  L
CGCCTACCTTCGTGGCAAGGCCATGGGTGAGGAATTCAACGACAAGGGCGTGGACATTTTGCTGGGGCCTGCTGCTGGTCCTCTCGGCAAATACCCGGAC 700
 A  Y  L  R  G  K  A  M  G  E  E  F  N  D  K  G  V  D  I  L  L  G  P  A  A  G  P  L  G  K  Y  P  D
GGCCGCAGAATCTGGGAAGGCTTCTCTCCTGATCCGGTTCTCACTGGTGTACTTTTCGCCGAAACTATCAAGGGTATCCAAGACGCGGGTGTGATTGCTA 800
 G  G  R  I  W  E  G  F  S  P  D  P  V  L  T  G  V  L  F  A  E  T  I  K  G  I  Q  D  A  G  V  I  A
CTGCCAAGCATTACATTCTGAATGAACAGGAGCATTTCCGACAGGTTGGCGAGGCCCAGGGATATGGTTACAACATCACGGAGACGATCAGCTCCAACGT 900
 T  A  K  H  Y  I  L  N  E  Q  E  H  F  R  Q  V  G  E  A  Q  G  Y  G  Y  N  I  T  E  T  I  S  S  N  V
GGATGACAAGACCATGCACGAGTTGTACCTTTGGTGAGTAGTTGACACTGCAAATGAGGACCTTGATTGATTTGACTGACCTGGAATGCAGGCCCTTTGC 1000
 D  D  K  T  M  H  E  L  Y  L  W                                                              P  F  A
AGATGCTGTGCGCGGTAAGATTTTCCGTACACTTGACCTCGCGACGAAGAAATCGCTGACGAACCATCGTAGCTGGCGTTGGCGCTGTCATGTGTTCCTA 1100
 D  A  V  R                                                                A  G  V  G  A  V  M  C  S  Y
CAATCAAATCAACAACAGCTACGGTTGTCAAAACAGTCAAACTCTCAACAAGCTCCTCAAGGCTGAGCTGGGCTTCCAAGGCTTCGTCATGAGTGACTGG 1200
 N  Q  I  N  N  S  Y  G  C  Q  N  S  Q  T  L  N  K  L  L  K  A  E  L  G  F  Q  G  F  V  M  S  D  W
AGCGCTCACCACAGCGGTGTCGGCGCTGCCCTCGCTGGGTTGGATATGTCGATGCCTGGAGACATTTCCTTCGACGACGGACTCTCCTTCTGGGGCACGA 1300
 S  A  H  H  S  G  V  G  A  A  L  A  G  L  D  M  S  M  P  G  D  I  S  F  D  D  G  L  S  F  W  G  T
ACCTAACTGTCAGTGTTCTTAACGGCACCGTTCCAGCCTGGCGTGTCGATGACATGGCTGTTCGTATCATGACCGCGTACTACAAGGTTGGTCGTGACCG 1400
 N  L  T  V  S  V  L  N  G  T  V  P  A  W  R  V  D  D  M  A  V  R  I  M  T  A  Y  Y  K  V  G  R  D  R
TCTTCGTATTCCCCCTAACTTCAGCTCCTGGACCCGGGATGAGTACGGCTGGGAGCATTCTGCTGTCTCCGAGGGAGCCTGACCAAGGTGAACGACTTC 1500
 L  R  I  P  P  N  F  S  S  W  T  R  D  E  Y  G  W  E  H  S  A  V  S  E  G  A  W  T  K  V  N  D  F
GTCAATGTGCAGCGCAGTCACTCTCAGATCATCCGTGAGATTGGTGCCGCTAGTACAGTGCTCTTGAAGAACACGGGTGCTCTTCCTTTGACCGGCAAGG 1600
 V  N  V  Q  R  S  H  S  Q  I  I  R  E  I  G  A  A  S  T  V  L  L  K  N  T  G  A  L  P  L  T  G  K
AGGTTAAAGTGGGTGTTCTCGGTGAAGACGCTGGTTCCAACCCGTGGGGTGCTAACGGCTGCCCCGACCGCGGCTGTGATAACGGCACTCTTGCTATGGC 1700
 E  V  K  V  G  V  L  G  E  D  A  G  S  N  P  W  G  A  N  G  C  P  D  R  G  C  D  N  G  T  L  A  M  A
CTGGGGTAGTGGTACTGCCAACTTCCCTTACCTTGTCACCCCCGAGCAGGCTATCCAGCGAGAGGTCATCAGCAACGGCGGCAATGTCTTTGCTGTGACT 1800
 W  G  S  G  T  A  N  F  P  Y  L  V  T  P  E  Q  A  I  Q  R  E  V  I  S  N  G  G  N  V  F  A  V  T
GATAACGGGCTCTCAGCCAGATGGCAGATGTTGCATCTCAATCCAGGTGAGTGCGGGCTCTTAGAAAAAGAACGTTCTCTGAATCAACTTTTTTAACCA 1900
 D  N  G  A  L  S  Q  M  A  D  V  A  S  Q  S  S
```

Fig. 1A

```
TTGCGAACAGCCTGTCTTTGGTGTTTGTCAACGCCGACTCTGGAGAGGGTTTCATCAGTGTCGACGGCAACGAGGGTGACCGCAAAAATCTCACTCTGTG 2000
            V  S  L  V  F  V  N  A  D  S  G  E  G  F  I  S  V  D  G  N  E  G  D  R  K  N  L  T  L  W
GAAGAACGGCGAGGCCGTCATTGACACTGTTGTCAGCCACTGCAACAACACGATTGTGGTTATTCACAGTGTTGGGCCCGTCTTGATCGACCGGTGGTAT 2100
     K  N  G  E  A  V  I  D  T  V  V  S  H  C  N  N  T  I  V  V  I  H  S  V  G  P  V  L  I  D  R  W  Y
GATAACCCCAACGTCACTGCCATCATCTGGGCCGGCTTGCCCGGTCAGGAGAGTGGCAACTCCCTGGTCGACGTGCTCTATGGCCGCGTCAACCCCAGCG 2200
     D  N  P  N  V  T  A  I  I  W  A  G  L  P  G  Q  E  S  G  N  S  L  V  D  V  L  Y  G  R  V  N  P  S
CCAAGACCCCGTTCACCTGGGGCAAGACTCGGGAGTCTTACGGGGCTCCCTTGCTCACCGAGCCTAACAATGGCAATGGTGCTCCCCAGGATGATTTCAA 2300
     A  K  T  P  F  T  W  G  K  T  R  E  S  Y  G  A  P  L  L  T  E  P  N  N  G  N  G  A  P  Q  D  D  F  N
CGAGGGCGTCTTCATTGACTACCGTCACTTTGACAAGCGCAATGAGACCCCCATTTATGAGTTTGGCCATGGCTTGAGCTACACCACCTTTGGTTACTCT 2400
      E  G  V  F  I  D  Y  R  H  F  D  K  R  N  E  T  P  I  Y  E  F  G  H  G  L  S  Y  T  T  F  G  Y  S
CACCTTCGGGTTCAGGCCCTCAATAGTTCCAGTTCGGCATATGTCCCGACTAGCGGAGAGACCAAGCCTGCCGCCAACCTATGGTGAGATCGGTAGTGCCG 2500
     H  L  R  V  Q  A  L  N  S  S  S  S  A  Y  V  P  T  S  G  E  T  K  P  A  P  T  Y  G  E  I  G  S  A
CCGACTACCTGTATCCCGAGGGTCTCAAAAGAATTACCAAGTTTATTTACCCTTGGCTCAACTCGACCGACCTCGAGGATTCTTCTGACGACCCGAACTA 2600
     A  D  Y  L  Y  P  E  G  L  K  R  I  T  K  F  I  Y  P  W  L  N  S  T  D  L  E  D  S  S  D  D  P  N  Y
CGGCTGGGAGGACTCGGAGTACATTCCCGAAGGCGCTAGGGATGGGTCTCCTCAACCCCTCCTGAAGGCTGGCGGCGCTCCTGGTGGTAACCCTACCCTT 2700
      G  W  E  D  S  E  Y  I  P  E  G  A  R  D  G  S  P  Q  P  L  L  K  A  G  G  A  P  G  G  N  P  T  L
TATCAGGATCTTGTTAGGGTGTCGGCCACCATAACCAACACTGGTAACGTCGCCGGTTATGAAGTCCCTCAATTGGTGAGTGACCCGCATGTTCCTTGCG 2800
     Y  Q  D  L  V  R  V  S  A  T  I  T  N  T  G  N  V  A  G  Y  E  V  P  Q  L
TTGCAATTTGGCTAACTCGCTTCTAGTATGTTCACTGGGCGGACCGAACGAGCCTCGGGTCGTTCTGCGCAAGTTCGACCGAATCTTCCTGGCTCCTGG 2900
                     Y  V  S  L  G  G  P  N  E  P  R  V  V  L  R  K  F  D  R  I  F  L  A  P  G
GGAGCAAAAGCTTTGGACCACGACTCTTAACCGTCGTGATCTCGCCAATTGGGATGTGGAGGCTCAGGACTGGGTCATCACAAAGTACCCCAAGAAAGTG 3000
     E  Q  K  V  W  T  T  T  L  N  R  R  D  L  A  N  W  D  V  E  A  Q  D  W  V  I  T  K  Y  P  K  K  V
CACGTCGGCAGCTCCTCGCGTAAGCTGCCTCTGAGAGCGCCTCTGCCCCGTGTCTACTAG 3060
     H  V  G  S  S  S  R  K  L  P  L  R  A  P  L  P  R  V  Y
```

Fig. 1B

POLYPEPTIDES HAVING BETA-GLUCOSIDASE ACTIVITY AND POLYNUCLEOTIDES ENCODING SAME

CROSS-REFERENCE TO RELATED APPLICATION

This application is a divisional of U.S. application Ser. No. 11/760,243, filed Jun. 8, 2007, now U.S. Pat. No. 7,670,819, which is a divisional of U.S. application Ser. No. 10/976,660, filed Oct. 28, 2004, now U.S. Pat. No. 7,244,605, which claims the benefit of U.S. Provisional Application No. 60/515,482, filed Oct. 28, 2003.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

BACKGROUND OF THE INVENTION

1. Field of the Invention

The present invention relates to isolated polypeptides having beta-glucosidase activity and isolated polynucleotides encoding the polypeptides. The invention also relates to nucleic acid constructs, vectors, and host cells comprising the polynucleotides as well as methods for producing and using the polypeptides.

2. Description of the Related Art

Cellulose is a polymer of the simple sugar glucose covalently bonded by beta-1,4-linkages. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of cellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is extremely undesirable for ethanol production.

Cellobiose accumulation has been a major problem in enzymatic hydrolysis because cellulase-producing microorganisms produce little beta-glucosidase. The low amount of beta-glucosidase results in a shortage of capacity to hydrolyze the cellobiose to glucose. Several approaches have been used to increase the amount of beta-glucosidase in cellulose conversion to glucose.

One approach is to produce beta-glucosidase using microorganisms that produce little cellulase, and add the beta-glucosidase exogenously to endoglucanase and cellobiohydrolase to enhance the hydrolysis. However, the quantities required are too costly for a commercial biomass to ethanol operation.

A second approach is to carry out cellulose hydrolysis simultaneously with fermentation of the glucose by yeast. This process is known as simultaneous saccharification and fermentation (SSF). In an SSF system, fermentation of the glucose removes it from solution. However, SSF systems are not yet commercially viable because the operating temperature for yeast of 28° C. is too low for the 50° C. conditions required.

A third approach to overcome the shortage of beta-glucosidase is to overexpress the beta-glucosidase in a host, thereby increasing the yield of beta-glucosidase.

Ximenes et al., 1996, *Current Microbiology* 32: 119-123; Hang and Woodams, 1994, *Lebensmittel-Wissenschaft and Technologie* 27: 587-589; and Kitpreechavanich et al., *Agricultural and Biological Chemistry* 50: 1703-1712, disclose beta-glucosidases from *Aspergililus fumigatus*.

It would be very advantageous in the art to use a thermostable beta-glucosidase for converting cellulosic materials to monosaccharides, disaccharides, and polysaccharides to improve process efficiency.

It is an object of the present invention to provide new polypeptides having beta-glucosidase activity and nucleic acid encoding the polypeptides.

SUMMARY OF THE INVENTION

The present invention relates to isolated polypeptides having beta-glucosidase activity selected from the group consisting of:

(a) a polypeptide having an amino acid sequence which has at least 85% identity with amino acids 20 to 863 of SEQ ID NO: 2;

(b) a polypeptide which is encoded by a nucleotide sequence which hybridizes under at least high stringency conditions with (i) nucleotides 58 to 2580 of SEQ ID NO: 1, (ii) the cDNA sequence contained in nucleotides 58 to 2580 of SEQ ID NO: 1, or (iii) a complementary strand of (i) or (ii); and (c) a variant comprising a conservative substitution, deletion, and/or insertion of one or more amino acids of amino acids 20 to 863 of SEQ ID NO: 2.

The present invention also relates to isolated polynucleotides encoding polypeptides having beta-glucosidase activity, selected from the group consisting of:

(a) a polynucleotide encoding a polypeptide having an amino acid sequence which has at least 85% identity with amino acids 20 to 863 of SEQ ID NO: 2;

(b) a polynucleotide having at least 85% identity with nucleotides 58 to 2580 of SEQ ID NO: 1; and (c) a polynucleotide which hybridizes under at least high stringency conditions with (i) nucleotides 58 to 2580 of SEQ ID NO: 1, (ii) the cDNA sequence contained in nucleotides 58 to 2580 of SEQ ID NO: 1, or (iii) a complementary strand of (i) or (ii).

The present invention also relates to nucleic acid constructs, recombinant expression vectors, and recombinant host cells comprising the polynucleotides.

The present invention also relates to methods for producing such polypeptides having beta-glucosidase activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to detergent compositions comprising the polypeptides having beta-glucosidase activity.

The present invention also relates to plants encoding the polypeptides having beta-glucosidase activity.

The present invention further relates to using the polypeptides having beta-glucosidase activity in the conversion of cellulosic materials to monosaccharides, disaccharides, and polysaccharides.

The present invention further relates to nucleic acid constructs comprising a gene encoding a protein, wherein the gene is operably linked to a nucleotide sequence encoding a signal peptide consisting of nucleotides 1 to 57 of SEQ ID NO: 1, wherein the gene is foreign to the first and second nucleotide sequences.

BRIEF DESCRIPTION OF THE FIGURES

FIGS. 1A and 1B show the genomic DNA sequence and the deduced amino acid sequence of an *Aspergillus fumigatus* beta-glucosidase (SEQ ID NOs: 1 and 2, respectively). The predicted signal peptide is underlined and predicted introns are italicized.

DEFINITIONS

Figure 2:
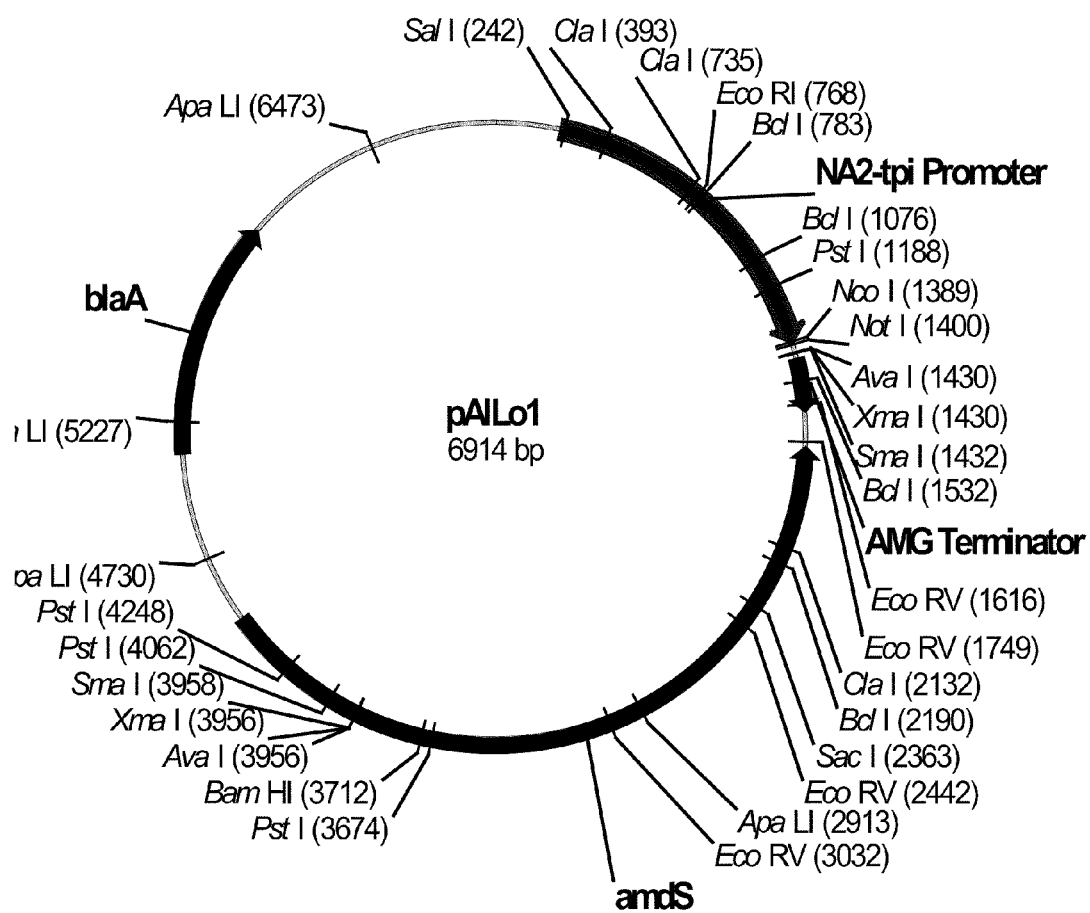
FIG. 2 shows a restriction map of pAlLo1.

Beta-glucosidase activity: The term "beta-glucosidase" is defined herein as a beta-D-glucoside glucohydrolase (E.C. 3.2.1.21) which catalyzes the hydrolysis of terminal non-reducing beta-D-glucose residues with the release of beta-D-glucose. For purposes of the present invention, beta-glucosidase activity is determined according to the basic procedure described by Venturi et al., 2002, *J. Basic Microbiol.* 42: 55-66, except different conditions were employed as described herein. One unit of beta-glucosidase activity is defined as 1.0 μmole of p-nitrophenol produced per minute at 50° C., pH 5 from 4 mM p-nitrophenyl-beta-D-glucopyranoside as substrate in 100 mM sodium citrate, 0.01% Tween-20.

Family GH3AA beta-glucosidase: The term "Family GH3AA beta-glucosidase" is defined herein as a glycoside hydrolase of Family 3 according to Coutinho, P. M. and Henrissat, B., 1999, Carbohydrate-active enzymes: an integrated database approach, in "*Recent Advances in Carbohydrate Bioengineering*", H. J. Gilbert, G. Davies, B. Henrissat and B. Svensson eds., The Royal Society of Chemistry, Cambridge, pp. 3-12.

The polypeptides of the present invention have at least 20%, at least 40%, more preferably at least 50%, more preferably at least 60%, more preferably at least 70%, more preferably at least 80%, even more preferably at least 90%, most preferably at least 95%, and even most preferably at least 100% of the beta-glucosidase activity of the polypeptide consisting of the amino acid sequence shown as amino acids 20 to 863 of SEQ ID NO: 2.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of SEQ ID NO: 2 or a homologous sequence thereof, wherein the fragment has beta-glucosidase activity. Preferably, a fragment contains at least 770 amino acid residues, more preferably at least 800 amino acid residues, and most preferably at least 830 amino acid residues.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having beta-glucosidase activity. Preferably, a subsequence contains at least 2310 nucleotides, more preferably at least 2400 nucleotides, and most preferably at least 2490 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the amino acids 20 to 863 of SEQ ID NO: 2 or a homologous sequence thereof as well as genetic manipulation of the DNA encoding that polypeptide. The modification can be substitutions, deletions and/or insertions of one or more amino acids as well as replacements of one or more amino acid side chains.

Artificial variant: When used herein, the term "artificial variant" means a polypeptide having beta-glucosidase activity produced by an organism expressing a modified nucleotide sequence of SEQ ID NO: 1 or a homologous sequence thereof, or the mature coding region thereof. The modified nucleotide sequence is obtained through human intervention by modification of the nucleotide sequence disclosed in SEQ ID NO: 1 or a homologous sequence thereof, or the mature coding region thereof.

DETAILED DESCRIPTION OF THE INVENTION

Polypeptides Having Beta-Glucosidase Activity

In a first aspect, the present invention relates to isolated polypeptides having an amino acid sequence which has a degree of identity to amino acids 20 to 863 of SEQ ID NO: 2 (i.e., the mature polypeptide) of at least 80%, more preferably at least 85%, even more preferably at least 90%, most preferably at least 95%, and even most preferably at least 97%, which have beta-glucosidase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 20 to 863 of SEQ ID NO: 2.

A polypeptide of the present invention preferably comprises the amino acid sequence of SEQ ID NO: 2 or an allelic variant thereof; or a fragment thereof that has beta-glucosidase activity. In a preferred aspect, a polypeptide comprises the amino acid sequence of SEQ ID NO: 2. In another preferred aspect, a polypeptide comprises amino acids 20 to 863 of SEQ ID NO: 2, or an allelic variant thereof; or a fragment thereof that has beta-glucosidase activity. In another preferred aspect, a polypeptide comprises amino acids 20 to 863 of SEQ ID NO: 2. In another preferred aspect, a polypeptide consists of the amino acid sequence of SEQ ID NO: 2 or an allelic variant thereof; or a fragment thereof that has beta-glucosidase activity. In another preferred aspect, a polypeptide consists of the amino acid sequence of SEQ ID NO: 2. In another preferred aspect, a polypeptide consists of amino acids 20 to 863 of SEQ ID NO: 2 or an allelic variant thereof; or a fragment thereof that has beta-glucosidase activity. In another preferred aspect, a polypeptide consists of amino acids 20 to 863 of SEQ ID NO: 2.

In a second aspect, the present invention relates to isolated polypeptides having beta-glucosidase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 58 to 2580 of SEQ ID NO: 1, (ii) the cDNA sequence contained in nucleotides 58 to 2580 of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has beta-glucosidase activity.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having beta-glucosidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having beta-glucosidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, the cDNA sequence contained in SEQ ID NO: 1, its complementary strand, or a subsequence thereof, under very low to very high stringency conditions. Molecules to which the nucleic acid probe hybridizes under these conditions can be detected using X-ray film.

In a preferred aspect, the nucleic acid probe is nucleotides 58 to 2580 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1 or its complementary strand. In another preferred aspect, the nucleic acid probe is the mature polypeptide coding region of SEQ ID NO: 1. In another preferred aspect, the nucleic acid probe is the polynucleotide sequence contained in plasmid pEJG113 which is contained in *Escherichia coli* NRRL B-30695, wherein the polynucleotide sequence thereof encodes a polypeptide having beta-glucosidase activity. In another preferred aspect, the nucleic acid probe is the mature polypeptide coding region contained in plasmid pEJG113 which is contained in *Escherichia coli* NRRL B-30695.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA*

48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of SEQ ID NO: 2 or a homologous sequence thereof; or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., beta-glucosidase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 20 to 863 of SEQ ID NO: 2 is 10, preferably 9, more preferably 8, more preferably 7, more preferably at most 6, more preferably 5, more preferably 4, even more preferably 3, most preferably 2, and even most preferably 1.

Sources of Polypeptides Having Beta-Glucosidase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a fungal polypeptide, and more preferably a yeast polypeptide such as a Candida, Kluyveromyces, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred aspect, the polypeptide is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis polypeptide having beta-glucosidase activity.

In another preferred aspect, the polypeptide is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum,

*Fusarium sporotrichioides, Fusarium sulphureum, Fusarium torulosum, Fusarium trichothecioides, Fusarium venenatum, Humicola Insolens, Humicola lanuginosa, Mucor mehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae* polypeptide.

In a more preferred aspect, the polypeptide is an *Aspergillus fumigatus* polypeptide, the polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in SEQ ID NO: 1. In another more preferred aspect, the nucleotide sequence is the sequence contained in plasmid pEJG113 that is contained in *Escherichia coli* NRRL B-30695. In another preferred aspect, the nucleotide sequence is the mature polypeptide coding region of SEQ ID NO: 1. In another more preferred aspect, the nucleotide sequence is the mature polypeptide coding region contained in plasmid pEJG113 that is contained in *Escherichia coli* NRRL B-30695. The present invention also encompasses nucleotide sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have beta-glucosidase activity.

The present invention also relates to mutant polynucleotides comprising at least one mutation in the mature polypeptide coding sequence of SEQ ID NO: 1, in which the mutant nucleotide sequence encodes a polypeptide which consists of amino acids 20 to 863 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 (i.e., nucleotides 58 to 2580) of at least 75%, more preferably at least 80%, more preferably at least 85%, more preferably at least 90%, even more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for beta-glucosidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 58 to 2580 of SEQ ID NO: 1, (ii) the cDNA sequence contained in nucleotides 58 to 2580 of SEQ ID NO: 1, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides 58 to 2580 of SEQ ID NO: 1, (ii) the cDNA sequence contained in nucleotides 58 to 2580 of SEQ ID NO: 1, or (iii) a complementary strand of (i) or (ii); and (b) isolating the hybridizing polynucleotide, which encodes a polypeptide having beta-glucosidase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide coding region is nucleotides 1 to 58 of SEQ ID NO: 1 which encode amino acids 1 to 19 of SEQ ID NO: 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1. (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Aspergillus*, and more preferably *Aspergillus fumigatus*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which consists of amino acids 20 to 863 of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Removal or Reduction of Beta-Glucosidase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred embodiment, the nucleotide sequence is disrupted with a selectable marker such as those described herein.

Alternatively, modification or inactivation of the nucleotide sequence may be performed by established anti-sense techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of beta-glucosidase activity by fermentation of a cell which produces both a polypeptide of the present invention as well as the protein product of interest by adding an effective amount of an agent capable of inhibiting beta-glucosidase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of beta-glucosidase activity by cultivating the cell under conditions permitting the expression of the product, subjecting the resultant culture broth to a combined pH and temperature treatment so as to reduce the beta-glucosidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a beta-glucosidase inhibitor.

In accordance with this aspect of the invention, it is possible to remove at least 60%, preferably at least 75%, more preferably at least 85%, still more preferably at least 95%, and most preferably at least 99% of the beta-glucosidase activity. Complete removal of beta-glucosidase activity may be obtained by use of this method.

The combined pH and temperature treatment is preferably carried out at a pH of 5 and a temperature of 70° C. for a sufficient period of time to attain the desired effect, where typically, 30 to 60 minutes is sufficient.

The methods used for cultivation and purification of the product of interest may be performed by methods known in the art.

The methods of the present invention for producing an essentially beta-glucosidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The beta-glucosidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-glucosidase activity which is produced by a method of the present invention.

Compositions

The present invention also relates to compositions comprising a polypeptide of the present invention. Preferably, the compositions are enriched in such a polypeptide. The term "enriched" indicates that the beta-glucosidase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus*

*fumigatus, Aspergillus foetidus, Aspergillus japonicus, Aspergillus nidulans, Aspergillus niger,* or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa*; or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Degradation of Biomass to Monosaccharides, Disaccharides, and Polysaccharides

The polypeptides having beta-glucosidase activity and host cells of the present invention may be used in the production of monosaccharides, disaccharides, and polysaccharides as chemical or fermentation feedstocks from biomass for the production of ethanol, plastics, or other products or intermediates. The polypeptides having beta-glucosidase activity may be in the form of a crude fermentation broth with or without the cells removed or in the form of a semi-purified or purified enzyme preparation. Alternatively, a host cell of the present invention may be used as a source of the polypeptide having beta-glucosidase activity in a fermentation process with the biomass.

Biomass can include, but is not limited to, wood resources, municipal solid waste, wastepaper, and crop residues (see, for example, Wiselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, *Recent Progress in Bioconversion of Lignocellulosics*, in *Advances in Biochemical Engineering/Biotechnology*, T. Scheper, managing editor, Volume 65, pp. 23-40, Springer-Verlag, New York).

The predominant polysaccharide in the primary cell wall of biomass is cellulose, the second most abundant is hemi-cellulose, and the third is pectin. The secondary cell wall, produced after the cell has stopped growing, also contains polysaccharides and is strengthened through polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

Three major classes of glycohydrolases are used to breakdown cellulosic biomass:

(1) The "endo-1,4-beta-glucanases" or 1,4-beta-D-glucan-4-glucanohydrolases (EC 3.2.1.4), which act randomly on soluble and insoluble 1,4-beta-glucan substrates.

(2) The "exo-1,4-beta-D-glucanases" including both the 1,4-beta-D-glucan glucohydrolases (EC 3.2.1.74), which liberate D-glucose from 1,4-beta-D-glucans and hydrolyze D-cellobiose slowly, and cellobiohydrolases (1,4-beta-D-glucan cellobiohydrolases, EC 3.2.1.91), which liberate D-cellobiose from 1,4-beta-glucans.

(3) The "beta-D-glucosidases" or beta-D-glucoside glucohydrolases (EC 3.2.1.21), which act to release D-glucose units from cellobiose and soluble cellodextrins, as well as an array of glycosides.

These three classes of enzymes work together synergistically resulting in efficient decrystallization and hydrolysis of native cellulose from biomass to yield reducing sugars.

The polypeptides having beta-glucosidase activity of the present invention may be used in conjunction with the above-noted enzymes to further degrade the cellulose component of the biomass substrate, (see, for example, Brigham et al., 1995, in *Handbook on Bioethanol* (Charles E. Wyman, editor), pp. 119-141, Taylor & Francis, Washington D.C.; Lee, 1997, *Journal of Biotechnology* 56: 1-24).

Ethanol can be produced by enzymatic degradation of biomass and conversion of the released saccharides to ethanol. This kind of ethanol is often referred to as bioethanol or biofuel. It can be used as a fuel additive or extender in blends of from less than 1% and up to 100% (a fuel substitute).

Detergent Compositions

The polypeptides having beta-glucosidase activity of the present invention may be added to and thus become a component of a detergent composition.

The detergent composition of the present invention may be, for example, formulated as a hand or machine laundry detergent composition including a laundry additive composition suitable for pre-treatment of stained fabrics and a rinse added fabric softener composition, or formulated as a detergent composition for use in general household hard surface cleaning operations, or formulated for hand or machine dishwashing operations.

In a specific aspect, the present invention provides a detergent additive comprising the polypeptides having beta-glucosidase activity of the present invention. The detergent additive as well as the detergent composition may comprise one or more other enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the enzymatic components should be compatible with the selected detergent, (i.e., pH-optimum, compatibility with other enzymatic and non-enzymatic ingredients, etc.), and the enzymatic components should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas lipase*, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus lipase*, e.g., from *B. subtilis* (Dartois et al., 1993, Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipases include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereas*, and variants thereof as those described in WO 93/24618, WO 95/10602, and WO 98/15257.

Commercially available peroxidases include Guardzyme™ (Novozymes A/S).

The enzymatic component(s) may be included in a detergent composition by adding separate additives containing one or more enzymes, or by adding a combined additive comprising all of these enzymes. A detergent additive of the present invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the present invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system that may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzymatic component(s) of the detergent composition of the present invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions any enzymatic component, in particular the polypeptides having beta-glucosidase activity of the present invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The polypeptides having beta-glucosidase activity of the present invention may additionally be incorporated in the detergent formulations disclosed in WO 97/07202 which is hereby incorporated as reference.

Plants

The present invention also relates to a transgenic plant, plant part, or plant cell which has been transformed with a nucleotide sequence encoding a polypeptide having beta-glucosidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napes*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having beta-glucosidase activity of the present invention under conditions conducive for production of the polypeptide; and (b) recovering the polypeptide.

Signal Peptide

The present invention also relates to nucleic acid constructs comprising a gene encoding a protein operably linked to a nucleotide sequence consisting of nucleotides 1 to 58 of SEQ ID NO: 1 encoding a signal peptide consisting of amino acids 1 to 19 of SEQ ID NO: 2, wherein the gene is foreign to the first and second nucleotide sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Aspergillus oryzae* Jal250 strain (WO 99/61651) was used for expression of the *Aspergillus fumigatus* beta-glucosidase. *Aspergillus fumigatus* PaHa34 was used as the source of the Family GH3A beta-glucosidase.

Media

PDA plates were composed per liter of 39 grams of potato dextrose agar.

MDU2BP medium was composed per liter of 45 g of maltose, 1 g of $MgSO_4 \cdot 7H_2O$, 1 g of NaCl, 2 g of $K_2SO_4$, 12 g of $KH_2PO_4$, 7 g of yeast extract, 2 g of urea, and 0.5 ml of AMG trace metals solution, pH to 5.0.

AMG trace metals solution was composed per liter of 14.3 g of $ZnSO_4 \cdot 7H_2O$, 2.5 g of $CuSO_4 \cdot 5H_2O$, 0.5 g of $NiCl_2 \cdot 6H_2O$, 13.8 g of $FeSO_4 \cdot 7H_2O$, 8.5 g of $MnSO_4 \cdot H_2O$, and 3 g of citric acid.

Cove plates were composed per liter of 342.3 g of sucrose, 20 ml of Cove salt solution, 10 ml of 1 M acetamide, 10 ml of 1.5 M $CsCl_2$, and 25 g of Noble agar.

Cove salt solution was composed per liter of 26 g of KCl, 26 g of $MgSO_4 \cdot 7H_2O$, 76 g of $KH_2PO_4$, and 50 ml of COVE trace metals solution.

Cove trace metals solution was composed per liter of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_2 \cdot 2H_2O$, and 10 g of $ZnSO_4 \cdot 7H_2O$.

CIM medium was composed per liter of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4 \cdot 7H_2O$, and 0.42 ml of trace metals solution, pH to 6.0.

Trace metals solution was composed per liter of 41.2 mg of $FeCl_3 \cdot 6H_2O$, 11.6 mg of $ZnSO_4 \cdot 7H_2O$, 5.4 mg of $MnSO_4 \cdot H_2O$, 2.0 mg of $CuSO_4 \cdot 5H_2O$, 0.48 mg of $H_3BO_3$, and 67.2 mg of citric acid.

Example 1

Identification of a Glycosyl Hydrolase Family GH3A Gene in the Genomic Sequence of *Aspergillus fumigatus*

A tblastn search (Altschul et al., 1997, *Nucleic Acids Res.* 25: 3389-3402) of the *Aspergillus fumigatus* partial genome sequence (The Institute for Genomic Research, Rockville, Md.) was carried out using as query a beta-glucosidase protein sequence from *Aspergillus aculeates* (Accession No. P48825). Several genes were identified as putative Family GH3A homologs based upon a high degree of similarity to the query sequence at the amino acid level. One genomic region of approximately 3000 by with greater than 70% identity to the query sequence at the amino acid level was chosen for further study.

Example 2

*Aspergillus fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA) and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated by using a Qiagen Maxi 500 column (QIAGEN Inc., Chatsworth, Calif.). The columns were equilibrated in 10 ml of QBT washed with 30 ml of QC, and eluted with 15 ml of QF (all buffers from QIAGEN Inc., Chatsworth, Calif.). DNA was precipitated in isopropanol, washed in 70% ethanol, and recovered by centrifugation. The DNA was resuspended in TE buffer.

Example 3

Construction of pAlLo2 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 by from the amdS selection marker by site-directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
AMDS3NcoMut (2050):                    (SEQ ID NO: 3)
5'-GTGCCCCATGATACGCCTCCGG-3'

AMDS2NcoMut (2721):                    (SEQ ID NO: 4)
5'-GAGTCGTATTTCCAAGGCTCCTGACC-3'

AMDS1NcoMut (3396):                    (SEQ ID NO: 5)
5'-GGAGGCCATGAAGTGGACCAACGG-3'
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to mutagenize the AMG terminator sequence:

```
                                       (SEQ ID NO: 6)
5'-CACCGTGAAAGCCATGCTCTTTCCTTCGTGTAGAAGAC
CAGACAG-3'
```

Lower Primer to mutagenize the AMG terminator sequence:

```
                                       (SEQ ID NO: 7)
5'-CTGGTCTTCTACACGAAGGAAAGAGCATGGCTTTCACG
GTGTCTG-3'
```

The last step in the modification of pBANe6 was the addition of a new Nco I restriction site at the beginning of the polylinker using a QuickChange Mutagenesis Kit and the following primers (underlined nucleotides represent the changed bases) to yield pAlLo1 (FIG. 2).

Upper Primer to mutagenize the NA2-tpi promoter:

```
                                       (SEQ ID NO: 8)
5'-CTATATACACAACTGGATTTACCATGGGCCCGCGGCCGCAGATC-3'
```

Lower Primer to mutagenize the NA2-tpi promoter:

```
                                       (SEQ ID NO: 9)
5'-GATCTGCGGCCGCGGGCCCATGGTAAATCCAGTTGTGTATATAG-3'
```

Figure 3:
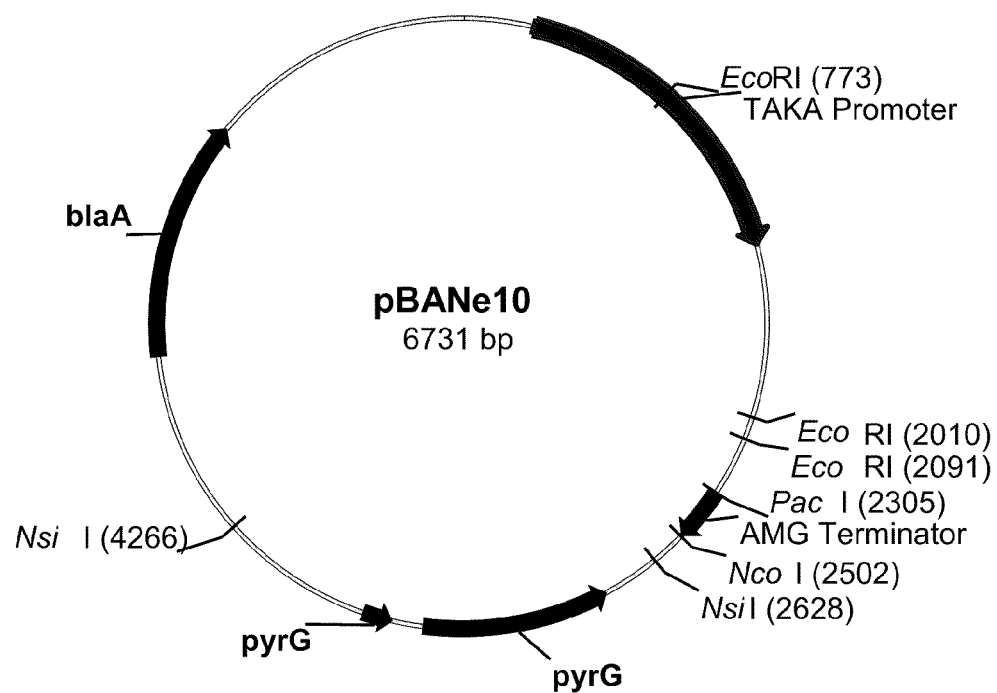
FIG. 3 shows a restriction map of pBANe10.
Figure 4:
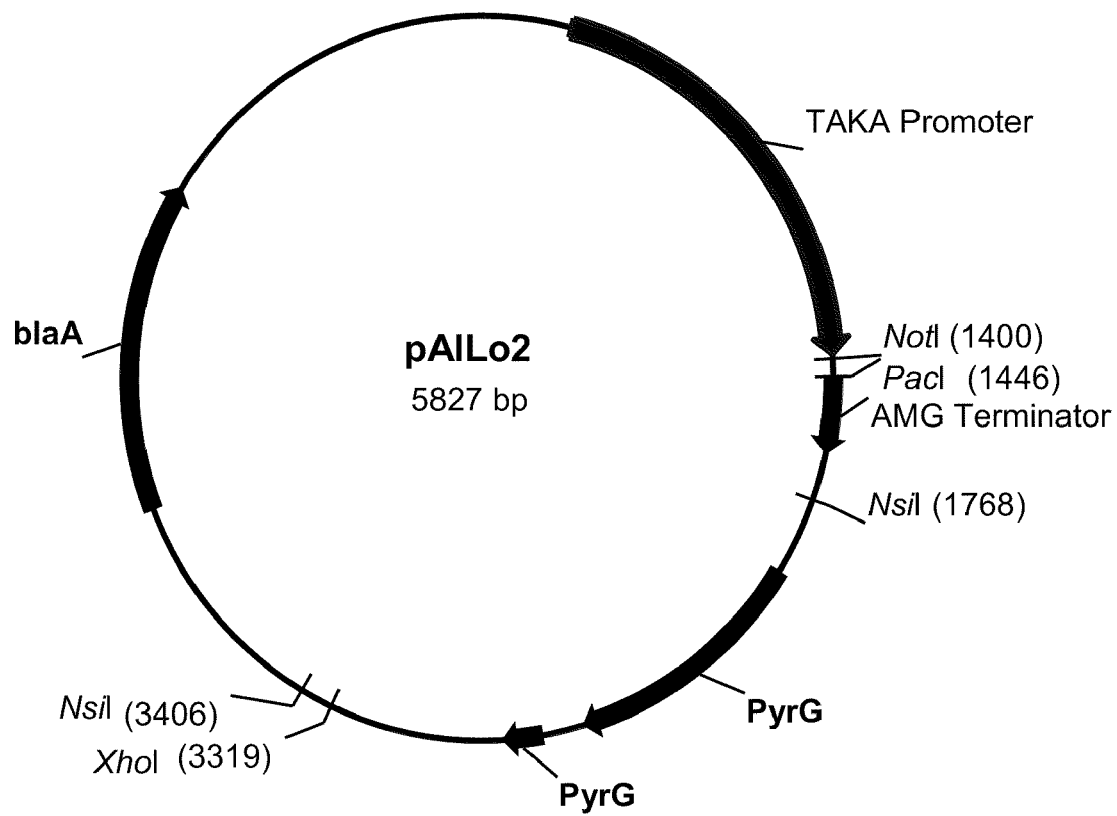
FIG. 4 shows a restriction map of pAlLo2.

The amdS gene of pAlLo1 was swapped with the *Aspergillus nidulans* pyrG gene. Plasmid pBANe10 (FIG. 3) was used as a source for the pyrG gene. Analysis of the sequence of pBANe10 showed that the pyrG marker was contained within an Nsi I restriction fragment and does not contain either Nco I or Pac I restriction sites. Since the amdS is also flanked by Nsi I restriction sites the strategy to switch the selection marker was a simple swap of Nsi I restriction fragments. Plasmid DNA from pAlLo1 and pBANe10 were digested with the restriction enzyme Nsi I and the products purified by agarose gel electrophoresis using standard procedures. The Nsi I fragment from pBANe10 containing the pyrG gene was ligated to the backbone of pAlLo1 to replace the original Nsi I DNA fragment containing the amdS gene. Recombinant clones were analyzed by restriction digest to determine whether they had the correct insert and correct orientation. A clone with the pyrG gene transcribed in the counterclockwise direction was selected. The new plasmid was designated pAlLo2 (FIG. 4).

Example 4

Cloning of the Family GH3A Beta-Glucosidase Gene and Construction of an *Aspergillus oryzae* Expression Vector Two synthetic oligonucleotide primers shown below were designed to PCR amplify a *Aspergillus fumigatus* gene encoding a putative Family GH3A beta-glucosidase from the genomic DNA prepared in Example 2. An InFusion Cloning Kit (BD Biosciences, Palo Alto, Calif.) was used to clone the fragment directly into the expression vector, pAlLo2, without the need for restriction digests and ligation.

```
Forward primer:
                                    (SEQ ID NO: 10)
5'-ACTGGATTTACCATGAGATTCGGTTGGCTCG-3'

Reverse primer:
                                    (SEQ ID NO: 11)
5'-AGTCACCTCTAGTTACTAGTAGACACGGGGC-3'
```

Bold letters represent coding sequence. The remaining sequence is homologous to the insertion sites of pAlLo2.

Fifty picomoles of each of the primers above were used in a PCR reaction containing 100 ng of *Aspergillus fumigatus* genomic DNA, 1×Pfx Amplification Buffer (Invitrogen, Carlsbad, Calif.), 1.5 µl of 10 mM blend of dATP, dTTP, dGTP, and dCTP, 2.5 units of Platinum Pfx DNA Polymerase (Invitrogen, Carlsbad, Calif.), 1 µl of 50 mM MgSO$_4$ and 2.5 µl of 10×pCRx Enhancer solution (Invitrogen, Carlsbad, Calif.) in a final volume of 50 µl. The amplification conditions were one cycle at 94° C. for 2 minutes; 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using 40 mM Tris base-20 mM sodium acetate-1 mM disodium EDTA (TAE) buffer where a 3 kb product band was excised from the gel and purified using a QIAquick Gel Extraction Kit (QIAGEN, Chatsworth, Calif.) according to the manufacturer's instructions.

Figure 5:
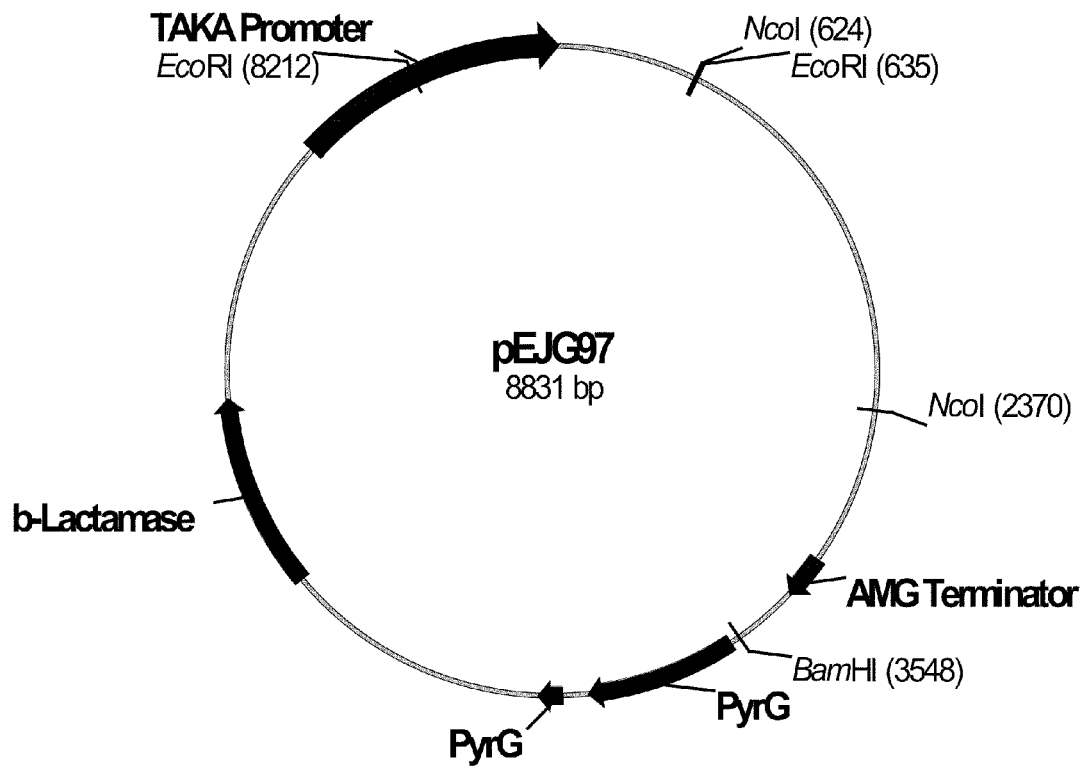
FIG. 5 shows a restriction map of pEJG97.

The fragment was then cloned into the pAlLo2 expression vector using an Infusion Cloning Kit. The vector was digested with restriction endonucleases Nco I and Pac I (using conditions specified by the manufacturer). The fragment was purified by gel electrophoresis and Qiaquick gel purification. The gene fragment and the cut vector were ligated together in a reaction resulting in the expression plasmid pEJG97 (FIG. 5) in which transcription of the Family GH3A beta-glucosidase gene was under the control of the NA2-tpi promoter. The ligation reaction (50 µl) was composed of 1× InFusion Buffer (BD Biosciences, Palo Alto, Calif.), 1×BSA (BD Biosciences, Palo Alto, Calif.), 1 µl of Infusion enzyme (diluted 1:10) (BD Biosciences, Palo Alto, Calif.), 150 ng of pAlLo2 digested with Nco I and Pac I, and 50 ng of the *Aspergillus fumigatus* beta-glucosidase purified PCR product. The reaction was incubated at room temperature for 30 minutes. One µl of the reaction was used to transform *E. coli* XL10 Solopac Gold cells (Stratagene, La Jolla, Calif.). An *E. coli* transformant containing the pEJG97 plasmid was detected by restriction digestion and plasmid DNA was prepared using a BioRobot 9600 (QIAGEN, Inc., Chatsworth, Calif.)

Example 5

Characterization of the Aspergillus Fumigatus Genomic Sequence Encoding a Family GH3A Beta-Glucosidase DNA sequencing of the *Aspergillus fumigatus* beta-glucosidase gene from pEJG97 was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

A gene model for the *Aspergillus fumigatus* sequence was constructed based on similarity to homologous genes from *Aspergillus aculeates, Aspergillus niger*, and *Aspergillus kawachii*. The nucleotide sequence (SEQ ID NO: 1) and deduced amino acid sequence (SEQ ID NO: 2) are shown in FIGS. 1A and 1B. The genomic fragment encodes a polypeptide of 863 amino acids, interrupted by 8 introns of 62, 55, 58, 63, 58, 58, 63 and 51 bp. The % G+C content of the gene is 54.3% and the mature coding region is 53.65%. Using the SignalP software program (Nielsen et al., 1997, *Protein Engineering* 10:1-6), a signal peptide of 19 residues was predicted. The predicted mature protein contains 844 amino acids with a molecular mass of 91.7 kDa.

A comparative alignment of beta-glucosidase sequences was determined using the Clustal W method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* beta-glucosidase gene shared 78%, 76%, and 76% identity to the deduced amino acid sequences of the *Aspergillus aculeatus* (accession number P48825), *Aspergillus niger* (O00089), and *Aspergillus kawachii* (P87076) beta-glucosidases.

Example 6

Expression of the *Aspergillus fumigatus* Family GH3A Beta-Glucosidase Gene in *Aspergillus oryzae* JAL250

*Aspergillus oryzae* Jal250 protoplasts were prepared according to the method of Christensen et al., 1988, *Bio/Technology* 6: 1419-1422. Five µg of pEJG97 (as well as pAlLo2 as a vector control) was used to transform *Aspergillus oryzae* JAL250.

The transformation of *Aspergillus oryzae* Jal250 with pEJG97 yielded about 100 transformants. Ten transformants were isolated to individual PDA plates.

Confluent PDA plates of five of the ten transformants were washed with 5 ml of 0.01% Tween 20 and inoculated separately into 25 ml of MDU2BP medium in 125 ml glass shake flasks and incubated at 34° C., 250 rpm. Five days after incubation, 0.5 µl of supernatant from each culture was analyzed using 8-16% Tris-Glycine SDS-PAGE gels (Invitrogen, Carlsbad, Calif.) according to the manufacturer's instructions. SDS-PAGE profiles of the cultures showed that one of the transformants (designated transformant 1) had a major band of approximately 130 kDa.

A confluent plate of transformant 1 (grown on PDA) was washed with 10 ml of 0.01% Tween 20 and inoculated into a 2 liter Fernbach containing 400 ml of MDU2BP medium to generate broth for characterization of the enzyme. The flask was harvested on day 5 and filtered using a 0.22 µm GP Express plus Membrane (Millipore, Bedford, Mass.).

Example 7

Construction of pMJ09

Vector pMJ04 was constructed by PCR amplifying the *Trichoderma reesei* Cel7A cellobiohydrolase 1 gene (cbh1) terminator from *Trichoderma reesei* RutC30 genomic DNA using primers 993429 (antisense) and 993428 (sense) shown below. The antisense primer was engineered to have a Pac I site at the 5'-end and a Spe I site at the 5'-end of the sense primer.

Primer 993429 (antisense):

```
                                    (SEQ ID NO: 12)
5'-AACGTTAATTAAGGAATCGTTTTGTGTTT-3'
```

Primer 993428 (sense):

```
                                    (SEQ ID NO: 13)
5'-AGTACTAGTAGCTCCGTGGCGAAAGCCTG-3'
```

The amplification reactions (50 µl) were composed of 1× ThermoPol Reaction Buffer (New England Biolabs, Beverly, Mass.), 0.3 mM dNTPs, 100 ng of *Trichoderma reesei* RutC30 genomic DNA (which was isolated using a DNeasy Plant Maxi Kit from Qiagen, Chatsworth, Calif.), 0.3 µM primer 993429, 0.3 µM primer 993428, and 2U Vent polymerase (New England Biolabs, Beverly, Mass.). The reactions were incubated in an Eppendorf Mastercycler 5333 (Hamburg, Germany) programmed as follows: 30 cycles each for 30 seconds at 94° C., 30 seconds at 55° C., and 30 seconds at 72° C. (15 minute final extension).

The reaction products were isolated on a 1.0% agarose gel using 40 mM Tris base-20 mM sodium acetate-1 mM disodium EDTA (TAE) buffer where a 229 by product band was excised from the gel and purified using a QIAGEN QIAquick Gel Extraction Kit according to the manufacturer's instructions.

Figure 6:
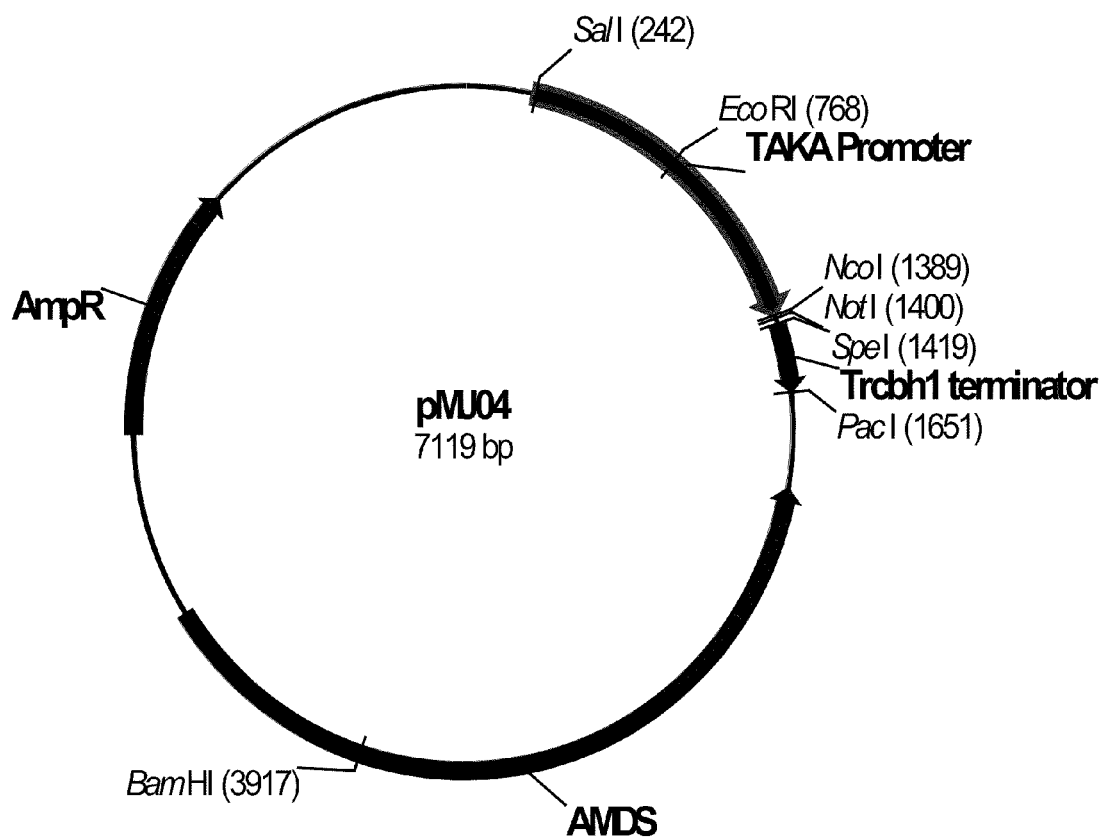
FIG. 6 shows a restriction map of pMJ04.

The resulting PCR fragment was digested with Pac I and Spe I and ligated into pAlLo1 digested with the same restriction enzymes using a Rapid Ligation Kit (Roche, Indianapolis, Ind.), to generate pMJ04 (FIG. 6).

Vector pMJ06 was constructed by PCR amplifying the *Trichoderma reesei* Cel7A cellobiohydrolase 1 gene (cbh1) promoter from *Trichoderma reesei* RutC30 genomic DNA using primers 993696 (antisense) and 993695 (sense) shown below. The antisense primer was engineered to have a Sal I site at the 5'-end of the sense primer and an Nco I site at the 5'-end of the antisense primer.

Primer 993695 (sense):

```
5'-ACTAGTCGACCGAATGTAGGATTGTT-3'   (SEQ ID NO: 14)
```

Primer 993696 (antisense):

```
5'-TGACCATGGTGCGCAGTCC-3'   (SEQ ID NO: 15)
```

The amplification reactions (50 µl) were composed of 1× ThermoPol Reaction Buffer, 0.3 mM dNTPs, 100 ng *Trichoderma reesei* RutC30 genomic DNA (which was prepared using a QIAGEN DNeasy Plant Maxi Kit), 0.3 µM primer 993696, 0.3 µM primer 993695, and 2U Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension).

The reaction products were isolated on a 1.0% agarose gel using TAE buffer where a 988 by product band was excised from the gel and purified using a QIAGEN QIAquick Gel Extraction Kit according to the manufacturer's instructions.

Figure 7:
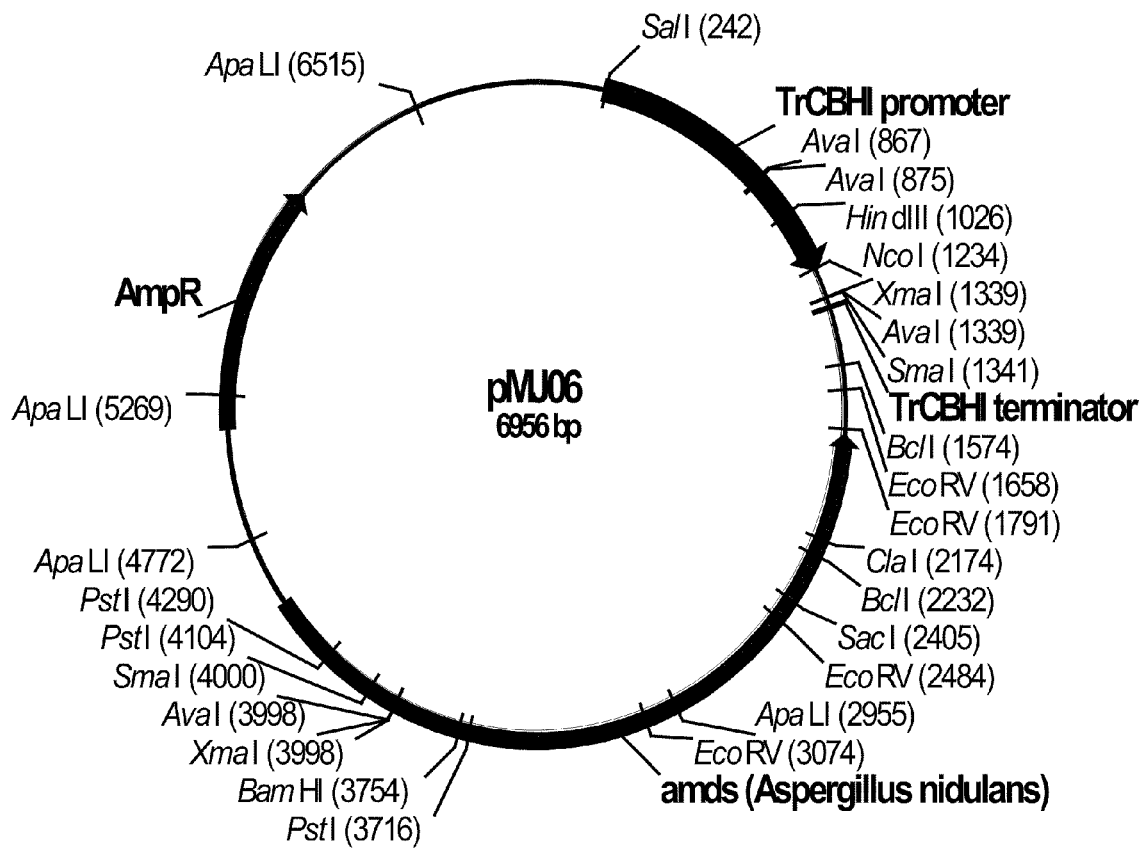
FIG. 7 shows a restriction map of pMJ06.

The resulting PCR fragment was digested with Nco I and Sal I and ligated into pMJ04 digested with the same restriction enzymes, using a Rapid Ligation Kit, to generate pMJ06 (FIG. 7). Expression vector pMJ09 was constructed by PCR amplifying the *Trichoderma reesei* Cel7A cellobiohydrolase 1 gene (cbh1) terminator from *Trichoderma reesei* RutC30 genomic DNA using primers 993843 (antisense) and 99344 (sense) shown below. The antisense primer was engineered to have a Pac I and a Spe I sites at the 5'-end and a Pvu I site at the 5'-end of the sense primer.

Primer 993844 (sense):

```
5'-CGATCGTCTCCCTATGGGTCATTACC-3'   (SEQ ID NO: 16)
```

Primer 993843 (antisense):

```
5'-ACTAGTTAATTAAGCTCCGTGGCGAAAG-3'   (SEQ ID NO: 17)
```

The amplification reactions (50 µl) were composed of 1× ThermoPol Reaction Buffer, 0.3 mM dNTPs, 100 ng of *Trichoderma reesei* RutC30 genomic DNA (which was extracted using a QIAGEN DNeasy Plant Maxi Kit), 0.3 µM primer 993844, 0.3 µM primer 993843, and 2U of Vent polymerase. The reactions were incubated in an Eppendorf Mastercycler 5333 programmed as follows: 30 cycles each for 30 seconds at 94° C., 30 seconds at 55° C., and 60 seconds at 72° C. (15 minute final extension).

The reaction products were isolated on a 1.0% agarose gel using TAE buffer where a 473 by product band was excised from the gel and purified using a QIAGEN QIAquick Gel Extraction Kit according to the manufacturer's instructions.

Figure 8:
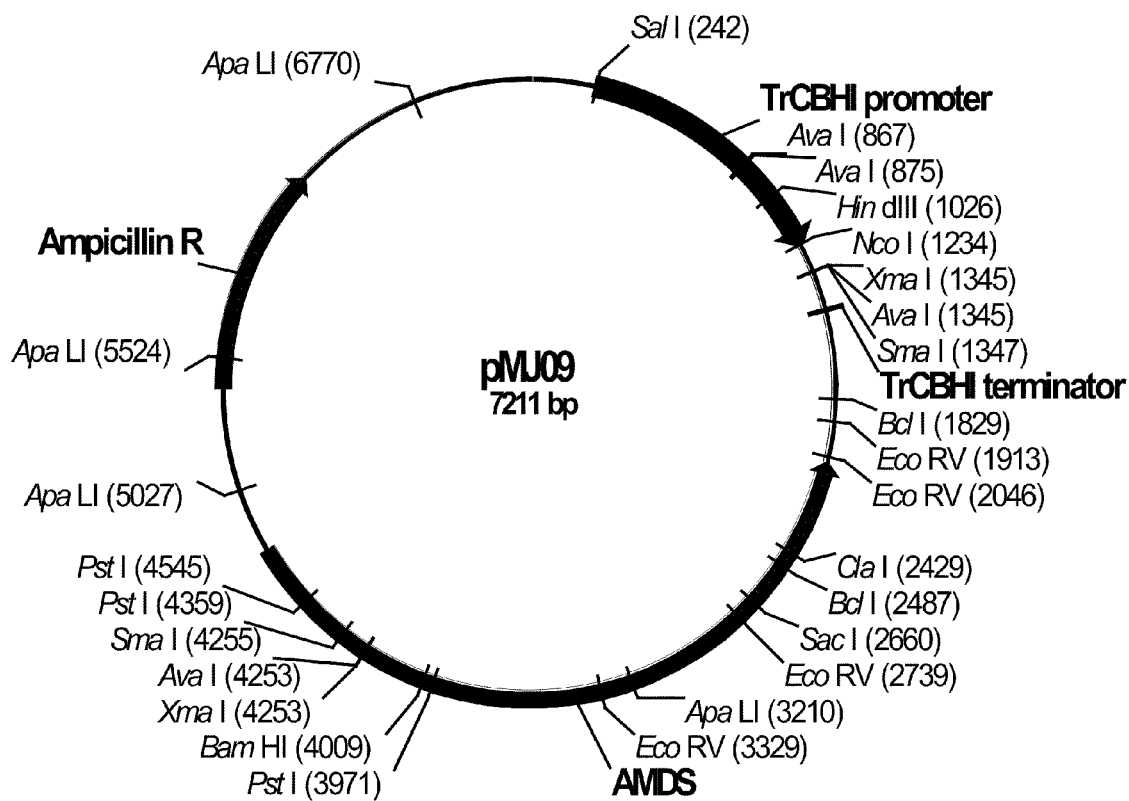
FIG. 8 shows a restriction map of pMJ09.

The resulting PCR fragment was digested with Pvu I and Spe I and ligated into pMJ06 digested with Pac I and Spe I using a Rapid Ligation Kit, to generate pMJ09 (FIG. 8).

Example 8

Expression of the *Aspergillus fumigatus* Family GH3A Beta-Glucosidase Gene in *Tricohoderma reesei*

Two synthetic oligonucleotide primers shown below were designed to PCR amplify the *Aspergillus fumigatus* beta-glucosidase gene from pEJG97 described in Example 4. An InFusion Cloning Kit was used to clone the fragment directly into the expression vector, pMJ09, without the need for restriction digests and ligation.

```
Forward primer:
                                    (SEQ ID NO: 18)
5'-GGACTGCGCACCATGAGATTCGGTTGGCTC-3'

Reverse primer:
                                    (SEQ ID NO: 19)
5'-TCGCCACGGAGCTTACTAGTAGACACGGGG-3'
```

Bold letters represent coding sequence. The remaining sequence was homologous to the insertion sites of pMJ09.

Fifty picomoles of each of the primers above were used in a PCR reaction (50 µl) containing 100 ng of pEJG97 DNA, 1× Pfx Amplification Buffer (Invitrogen, Carlsbad, Calif.), 1.5 µl of 10 mM blend of dATP, dTTP, dGTP, and dCTP, 2.5 units of Platinum Pfx DNA Polymerase (Invitrogen, Carlsbad, Calif.), 1 µl of 50 mM $MgSO_4$ and 2.5 µl of 10× pCRx Enhancer solution (Invitrogen, Carlsbad, Calif.). The amplification conditions were one cycle at 94° C. for 2 minutes; and 30 cycles each at 94° C. for 15 seconds, 55° C. for 30 seconds, and 68° C. for 3 minutes. The heat block then went to a 4° C. soak cycle.

The reaction products were isolated on a 1.0% agarose gel using TAE buffer where a 3 kb product band was excised from the gel and purified using a QIAGEN QIAquick Gel Extraction Kit according to the manufacturer's instructions.

Figure 9:
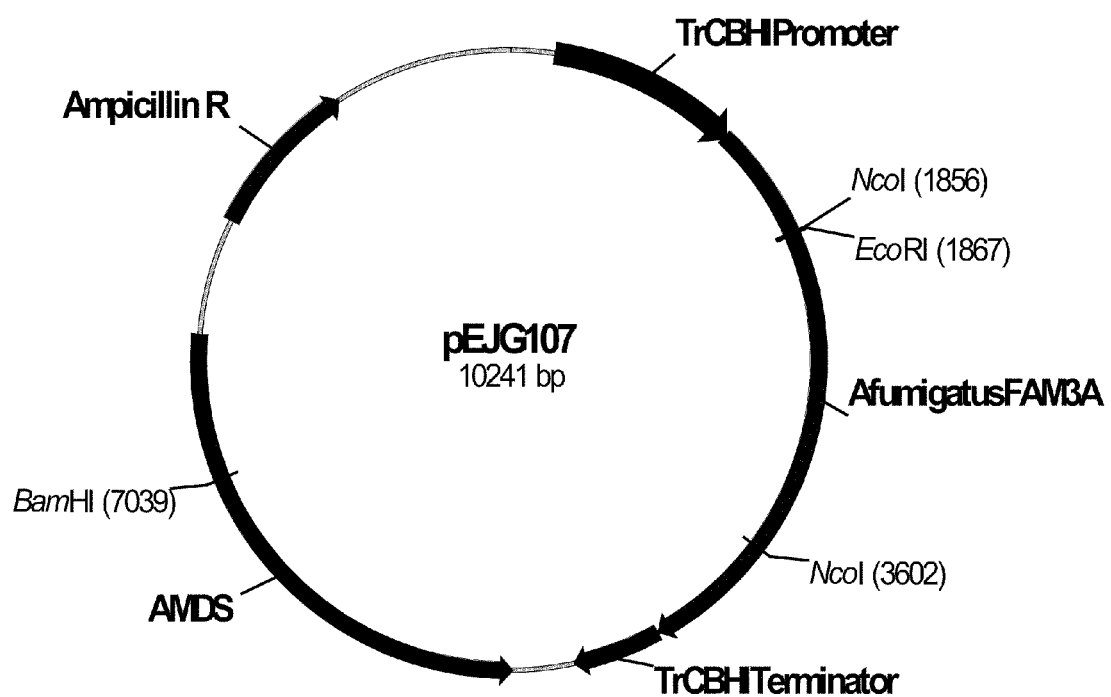
FIG. 9 shows a restriction map of pEJG107.

The purified 3 kb fragment was then cloned into pMJ09 using an Infusion Cloning Kit. The vector was digested with Nco I and Pac I. The fragment was purified by gel electrophoresis and Qiaquick gel purification, as described above. The gene fragment and the digested vector were ligated together in a reaction resulting in the expression plasmid pEJG107 (FIG. 9) in which transcription of the Family GH3A beta-glucosidase gene was under the control of the *Trichoderma reesei* cbhI promoter. The ligation (50 μl) was composed of lx InFusion Buffer, 1×BSA, 1 μl of Infusion enzyme (diluted 1:10), 100 ng of pMJ09 digested with Nco I and Pac I, and 100 ng of the *Aspergillus fumigatus* beta-glucosidase purified PCR product. The reaction was incubated at room temperature for 30 minutes. One μl of the reaction was used to transform *E. coli* electrompetent SURE cells (Stratagene, La Jolla, Calif.). An *E. coli* transformant containing the pEJG107 plasmid was detected by restriction digestion and plasmid DNA was prepared using a BioRobot 9600 (QIAGEN, Inc., Chatsworth, Calif.)

DNA sequencing of the *Aspergillus fumigatus* beta-glucosidase gene from pEJG107 was done with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

*Trichoderma reesei* RutC30 protoplasts were prepared according to the method of Christensen et al., 1988, supra. Five μg of pEJG107 were used to transform *Trichoderma reesei* RutC30. The transformation yielded about 100 transformants. Sixty transformants were isolated to individual Cove/10 mM uridine plates and incubated at 28° C.

Spores were collected from plates from 8 of the 60 transformants swiping three times with a sterile loop and inoculated separately into 25 ml of CIM medium in 125 ml glass shake flasks and incubated at 28° C., 250 rpm. Five days after incubation, 0.5 μl of supernatant from each culture was analyzed using 7.5% Tris SDS-PAGE gels (Biorad, Hercules, Calif.) according to the manufacturer's instructions. SDS-PAGE profiles of the cultures showed that one of the transformants (designated transformant 1) had a major band of approximately 130 kDa.

Example 9

Characterization of *Aspergillus fumigatus* Beta-Glucosidase

A 3 ml aliquot of the *Aspergillus fumigatus* beta-glucosidase, obtained as described in Example 6, was desalted using a BioRad Econo-Pac 10DG desalting column (BioRad, Hercues, Calif.), resulting in approx. 4 ml of desalted broth in 100 mM sodium citrate pH 5.0. The desalted broth was then concentrated to approximately 180 μl using an Amicon Centricon Plus-20 (Biomax-5, 5 kD cutoff, PES membrane) and diluted with 100 mM sodium citrate pH 5.0 to a final volume of approximately 500 μl. BCA assay (Smith et al., 1985, *Anal. Biochem.* 150: 76-85) of the desalted, concentrated broth showed a concentration of 1.00 mg of protein per ml. A second aliquot was also desalted to obtain more material, which yielded similar results.

SDS-PAGE (BioRad Criterion 7.5% Tris-HCl) of the concentrated desalted samples showed a major band at approx. 130 kD. The major band at 130 kD was cut out of the gel and submitted to N-terminal amino acid sequencing.

The *Aspergillus fumigatus* beta-glucosidase from the desalted/concentrated broth was evaluated for thermal stability at 50°, 65°, and 70° C. Assay conditions at 50° and 65° C. were: 100 mM sodium citrate pH 5.0, 0.01% Tween-20, 4 mM p-nitrophenyl-beta-D-glucopyranoside, [protein]$_{AfumGH3A}$= 6.9×10$^{-6}$ mg/ml, incubated at 50° and 65° C. Aliquots were taken at 0.5, 1, 2, 3, 3.75, and 24 hours. To each aliquot was added 1 M sodium carbonate pH 10.0, and the p-nitrophenyl anion concentration was determined from the absorbance at 405 nm. At 70° C., the assay conditions were: 100 mM sodium citrate (pH 5.0), 0.01% Tween-20, 4 mM p-nitrophenyl-beta-D-glucopyranoside, [protein]= 5.6×10$^{-6}$ mg/ml. Aliquots were taken at 0.25, 0.5, 1, 2, 4, and 5 hours. To each aliquot was added 1 M sodium carbonate pH 10.0, and the p-nitrophenyl anion concentration was determined from the absorbance at 405 nm. Note that each of the above protein concentrations refers to total protein concentration in the assay, as they were all assayed as broths rather than purified enzymes.

Figure 10:
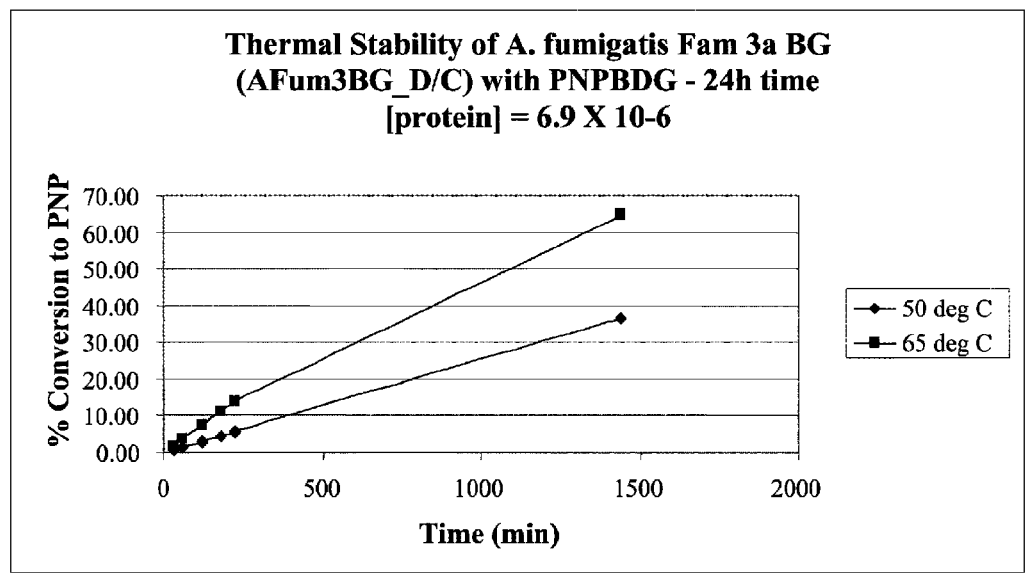
FIG. 10 shows the thermal stability of *Aspergillus fumigatus* beta-glucosidase at 50° and 65° C.
Figure 11:
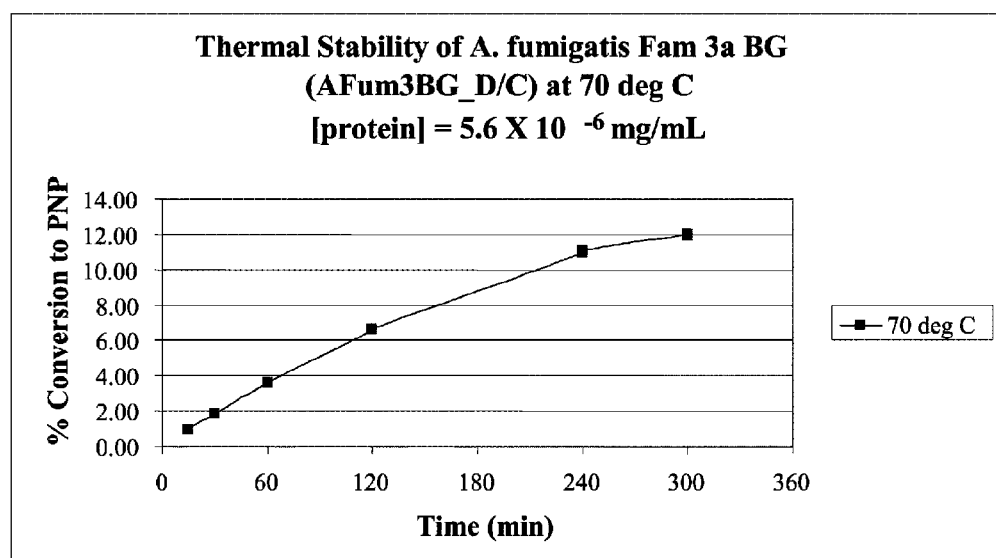
FIG. 11 shows the thermal stability of *Aspergillus fumigatus* beta-glucosidase at 70° C.

The results are shown in FIGS. 10 and 11. Thermal stability was defined as linear reaction kinetics for a given time interval, within a reasonable percent conversion (<15%) to p-nitrophenyl anion. The *Aspergillus fumigatus* beta-glucosidase appeared to be stable at least 24 hours at 50° C., although there were no time points between 4 hours and 24 hours. At 65° C. it appeared to be stable at least 3.75 hours, but afterward the stability gradually decreased with a 65% conversion to p-nitrophenyl anion at 24 hours. This conversion was quite high, so some of the observed decrease in rate may have been due to depletion of substrate and/or product inhibition in addition to possible thermal inactivation. At 70° C. it appeared to be stable for 1 hour, and reasonably stable to 2 hours.

Figure 12:
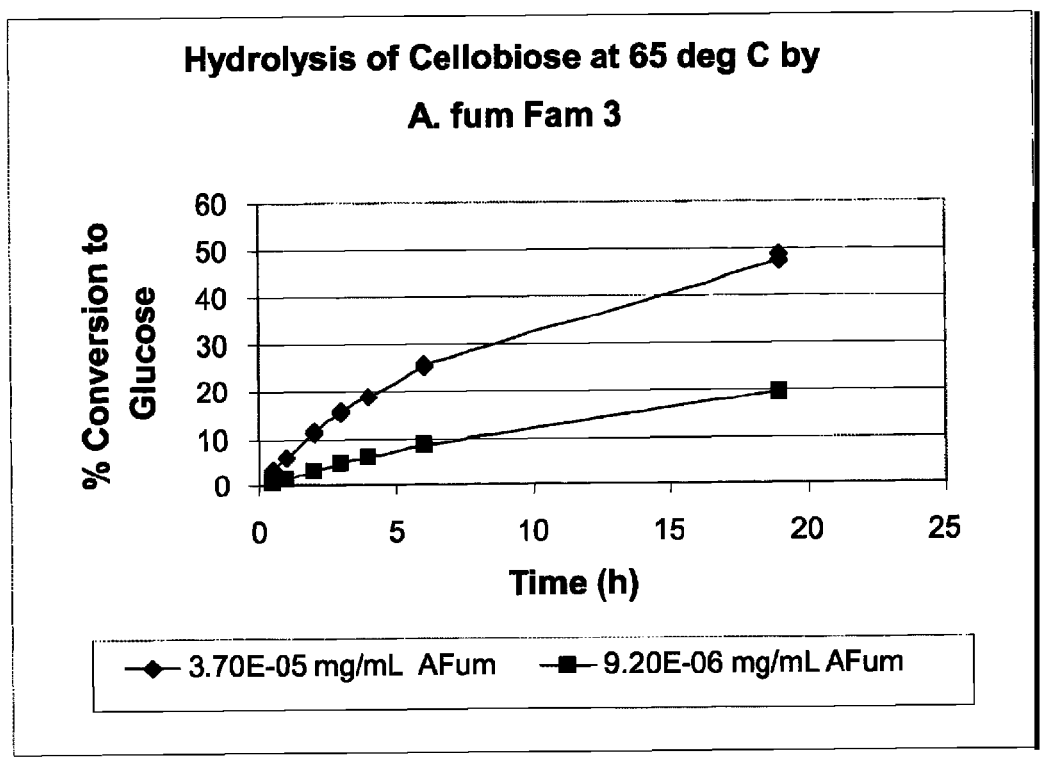
FIG. 12 shows the hydrolysis of cellobiose by *Aspergillus fumigatus* beta-glucosidase at 65° C.

Broth containing Family GH3A beta-glucosidase from *Aspergillus fumigatus*, obtained as described in Example 6, was first desalted (BioRad Econo-Pac 10DG column) and concentrated (Centricon Plus-20, Biomax-5, 5 kD cut-off), to a concentration of 0.92 mg/ml (BCA assay). Then, it was incubated at 0.037 and 0.0092 μg/ml total protein with 10 mM cellobiose in 100 mM sodium citrate pH 5.0 plus 0.01% Tween-20 at 65° C. Aliquots were taken at 0.5, 1, 2, 3, 4, 6, and 19 hours. Aliquots were boiled 6 minutes to terminate the reaction, and the glucose concentration determined using the Trinder assay (Sigma Chemical Co., St. Louis, Mo.) and external glucose standards. Results are shown in FIG. 12. The beta-glucosidase appeared to maintain 90% of its activity to 6 hours, and 65% to 19 hours at 65° C. at the lower protein loading (0.0092 μg/ml). The beta-glucosidase appeared to be reasonably stable up to 6 hours at 65° C.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* TOP10 (pEJG113) | NRRL B-30695 | Oct. 17, 2003 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

---

What is claimed is:

1. A method for degrading cellulose- and hemicellulose-containing biomass, comprising treating the biomass with an effective amount of a polypeptide having beta-glucosidase activity and recovering the degraded biomass, wherein the polypeptide having beta-glucosidase activity is selected from the group consisting of:

(a) a polypeptide comprising an amino acid sequence which has at least 95% identity with amino acids 20 to 863 of SEQ ID NO: 2; and (b) a polypeptide which is encoded by a polynucleotide which hybridizes under at least high stringency conditions with (i) nucleotides 58 to 2580 of SEQ ID NO: 1, (ii) the cDNA sequence contained in nucleotides 58 to 2580 of SEQ ID NO: 1, or (iii) the complement of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.

2. The method of claim 1, wherein the polypeptide having beta-glucosidase activity comprises an amino acid sequence which has at least 95% identity with amino acids 20 to 863 of SEQ ID NO: 2.

3. The method of claim 2, wherein the polypeptide having beta-glucosidase activity comprises an amino acid sequence which has at least 97% identity with amino acids 20 to 863 of SEQ ID NO: 2.

4. The method of claim 1, wherein the polypeptide having beta-glucosidase activity comprises the amino acid sequence of SEQ ID NO: 2.

5. The method of claim 1, wherein the polypeptide having beta-glucosidase activity consists of SEQ ID NO: 2 or a fragment thereof having beta-glucosidase activity.

6. The method of claim 5, wherein the polypeptide having beta-glucosidase activity consists of amino acids 20 to 863 of SEQ ID NO: 2.

7. The method of claim 1, wherein the polypeptide having beta-glucosidase activity is encoded by a polynucleotide which hybridizes under at least high stringency conditions with (i) nucleotides 58 to 2580 of SEQ ID NO: 1, (ii) the cDNA sequence contained in nucleotides 58 to 2580 of SEQ ID NO: 1, or (iii) the full-length complement of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 65° C.

8. The method of claim 7, wherein the polypeptide having beta-glucosidase activity is encoded by a polynucleotide which hybridizes under at least very high stringency conditions with (i) nucleotides 58 to 2580 of SEQ ID NO: 1, (ii) the cDNA sequence contained in nucleotides 58 to 2580 of SEQ ID NO: 1, or (iii) the full-length complement of (i) or (ii), wherein high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 70° C.

9. The method of claim 1, wherein the polypeptide having beta-glucosidase activity is encoded by the polynucleotide contained in plasmid pEJG113 which is contained in *E. coli* NRRL B-30695.

* * * * *

SEQUENCE LISTING

<160> NUMBER OF SEQ ID NOS: 19

<210> SEQ ID NO 1
<211> LENGTH: 3060
<212> TYPE: DNA
<213> ORGANISM: Aspergillus fumigatus

<400> SEQUENCE: 1

```
atgagattcg gttggctcga ggtggccgct ctgacggccg cttctgtagc caatgcccag        60
gtttgtgatg ctttcccgtc attgtttcgg atatagttga caatagtcat ggaaataatc       120
aggaattggc tttctctcca ccattctacc cttcgccttg ggctgatggc cagggagagt       180
gggcagatgc ccatcgacgc gccgtcgaga tcgtttctca gatgacactg gcggagaagg       240
ttaaccttac aacgggtact gggtgggttg cgacttttt gttgacagtg agctttcttc        300
actgaccatc tacacagatg ggaaatggac cgatgcgtcg gtcaaaccgg cagcgttccc       360
aggtaagctt gcaattctgc aacaacgtgc aagtgtagtt gctaaaacgc ggtggtgcag       420
acttggtatc aactggggtc tttgtggcca ggattcccct ttgggtatcc gtttctgtga       480
gctatacccg cggagtcttt cagtccttgt attatgtgct gatgattgtc tctgtatagc       540
tgacctcaac tccgccttcc ctgctggtac taatgtcgcc gcgacatggg acaagacact       600
cgcctacctt cgtggcaagg ccatgggtga ggaattcaac gacaagggcg tggacatttt       660 gctgggcct gctgctggtc ctctcggcaa atacccggac ggcggcagaa tctgggaagg       720
cttctctcct gatccggttc tcactggtgt acttttcgcc gaaactatca agggtatcca       780
agacgcgggt gtgattgcta ctgccaagca ttacattctg aatgaacagg agcatttccg       840
acaggttggc gaggcccagg gatatggtta caacatcacg gagacgatca gctccaacgt       900
ggatgacaag accatgcacg agttgtacct ttggtgagta gttgacactg caaatgagga       960
ccttgattga tttgactgac ctggaatgca ggcccttttgc agatgctgtg cgcggtaaga      1020 tttccgtag acttgacctc gcgacgaaga aatcgctgac gaaccatcgt agctggcgtt       1080
ggcgctgtca tgtgttccta caatcaaatc aacaacagct acggttgtca aaacagtcaa      1140
actctcaaca agctcctcaa ggctgagctg ggcttccaag gcttcgtcat gagtgactgg      1200
agcgctcacc acagcggtgt cggcgctgcc ctcgctgggt tggatatgtc gatgcctgga      1260
gacatttcct tcgacgacgg actctccttc tggggcacga acctaactgt cagtgttctt      1320
aacggcaccg ttccagcctg gcgtgtcgat gacatggctg ttcgtatcat gaccgcgtac      1380
tacaaggttg gtcgtgaccg tcttcgtatt cccctaact tcagctcctg gacccgggat      1440
gagtacggct gggagcattc tgctgtctcc gagggagcct ggaccaaggt gaacgacttc      1500
gtcaatgtgc agcgcagtca ctctcagatc atccgtgaga ttggtgccgc tagtacagtg      1560
ctcttgaaga acacgggtgc tcttcctttg accggcaagg aggttaaagt gggtgttctc      1620
```

-continued

```
ggtgaagacg ctggttccaa cccgtggggt gctaacggct gccccgaccg cggctgtgat    1680
aacggcactc ttgctatggc ctggggtagt ggtactgcca acttccctta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccct cctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgaccccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc tctgccccg tgtctactag     3060
```

<210> SEQ ID NO 2
<211> LENGTH: 863
<212> TYPE: PRT
<213> ORGANISM: Aspergillus fumigatus

<400> SEQUENCE: 2

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125
```

-continued

```
Met Gly Glu Glu Phe Asn Asp Lys Gly Val Asp Ile Leu Leu Gly Pro
            130                 135                 140
Ala Ala Gly Pro Leu Gly Lys Tyr Pro Asp Gly Arg Ile Trp Glu
145                 150                 155                 160
Gly Phe Ser Pro Asp Pro Val Leu Thr Gly Val Leu Phe Ala Glu Thr
                    165                 170                 175
Ile Lys Gly Ile Gln Asp Ala Gly Val Ile Ala Thr Ala Lys His Tyr
                180                 185                 190
Ile Leu Asn Glu Gln Glu His Phe Arg Gln Val Gly Glu Ala Gln Gly
                195                 200                 205
Tyr Gly Tyr Asn Ile Thr Glu Thr Ile Ser Ser Asn Val Asp Asp Lys
    210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                    245                 250                 255
Gly Cys Gln Asn Ser Gln Thr Leu Asn Lys Leu Leu Lys Ala Glu Leu
                260                 265                 270
Gly Phe Gln Gly Phe Val Met Ser Asp Trp Ser Ala His His Ser Gly
                275                 280                 285
Val Gly Ala Ala Leu Ala Gly Leu Asp Met Ser Met Pro Gly Asp Ile
    290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                    325                 330                 335
Arg Ile Met Thr Ala Tyr Tyr Lys Val Gly Arg Asp Arg Leu Arg Ile
                340                 345                 350
Pro Pro Asn Phe Ser Ser Trp Thr Arg Asp Glu Tyr Gly Trp Glu His
                355                 360                 365
Ser Ala Val Ser Glu Gly Ala Trp Thr Lys Val Asn Asp Phe Val Asn
    370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
                435                 440                 445
Ala Trp Gly Ser Gly Thr Ala Asn Phe Pro Tyr Leu Val Thr Pro Glu
    450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
                485                 490                 495
Ser Ser Val Ser Leu Val Phe Val Asn Ala Asp Ser Gly Glu Gly Phe
                500                 505                 510
Ile Ser Val Asp Gly Asn Glu Gly Asp Arg Lys Asn Leu Thr Leu Trp
                515                 520                 525
Lys Asn Gly Glu Ala Val Ile Asp Thr Val Val Ser His Cys Asn Asn
    530                 535                 540
Thr Ile Val Val Ile His Ser Val Gly Pro Val Leu Ile Asp Arg Trp
```

```
                545                 550                 555                 560
Tyr Asp Asn Pro Asn Val Thr Ala Ile Ile Trp Ala Gly Leu Pro Gly
                    565                 570                 575
Gln Glu Ser Gly Asn Ser Leu Val Asp Val Leu Tyr Gly Arg Val Asn
                580                 585                 590
Pro Ser Ala Lys Thr Pro Phe Thr Trp Gly Lys Thr Arg Glu Ser Tyr
            595                 600                 605
Gly Ala Pro Leu Leu Thr Glu Pro Asn Asn Gly Asn Gly Ala Pro Gln
            610                 615                 620
Asp Asp Phe Asn Glu Gly Val Phe Ile Asp Tyr Arg His Phe Asp Lys
625                 630                 635                 640
Arg Asn Glu Thr Pro Ile Tyr Glu Phe Gly His Gly Leu Ser Tyr Thr
                    645                 650                 655
Thr Phe Gly Tyr Ser His Leu Arg Val Gln Ala Leu Asn Ser Ser Ser
                660                 665                 670
Ser Ala Tyr Val Pro Thr Ser Gly Glu Thr Lys Pro Ala Pro Thr Tyr
            675                 680                 685
Gly Glu Ile Gly Ser Ala Ala Asp Tyr Leu Tyr Pro Glu Gly Leu Lys
            690                 695                 700
Arg Ile Thr Lys Phe Ile Tyr Pro Trp Leu Asn Ser Thr Asp Leu Glu
705                 710                 715                 720
Asp Ser Ser Asp Asp Pro Asn Tyr Gly Trp Glu Asp Ser Glu Tyr Ile
                    725                 730                 735
Pro Glu Gly Ala Arg Asp Gly Ser Pro Gln Pro Leu Leu Lys Ala Gly
                740                 745                 750
Gly Ala Pro Gly Gly Asn Pro Thr Leu Tyr Gln Asp Leu Val Arg Val
            755                 760                 765
Ser Ala Thr Ile Thr Asn Thr Gly Asn Val Ala Gly Tyr Glu Val Pro
            770                 775                 780
Gln Leu Tyr Val Ser Leu Gly Gly Pro Asn Glu Pro Arg Val Val Leu
785                 790                 795                 800
Arg Lys Phe Asp Arg Ile Phe Leu Ala Pro Gly Glu Gln Lys Val Trp
                    805                 810                 815
Thr Thr Thr Leu Asn Arg Arg Asp Leu Ala Asn Trp Asp Val Glu Ala
                820                 825                 830
Gln Asp Trp Val Ile Thr Lys Tyr Pro Lys Lys Val His Val Gly Ser
            835                 840                 845
Ser Ser Arg Lys Leu Pro Leu Arg Ala Pro Leu Pro Arg Val Tyr
            850                 855                 860

<210> SEQ ID NO 3
<211> LENGTH: 22
<212> TYPE: DNA
<213> ORGANISM: Aspergillus niger

<400> SEQUENCE: 3
gtgccccatg atacgcctcc gg                                              22

<210> SEQ ID NO 4
<211> LENGTH: 26
<212> TYPE: DNA
<213> ORGANISM: Aspergillus niger

<400> SEQUENCE: 4
gagtcgtatt tccaaggctc ctgacc                                          26
```

```
<210> SEQ ID NO 5
<211> LENGTH: 24
<212> TYPE: DNA
<213> ORGANISM: Aspergillus niger

<400> SEQUENCE: 5
ggaggccatg aagtggacca acgg                                            24

<210> SEQ ID NO 6
<211> LENGTH: 45
<212> TYPE: DNA
<213> ORGANISM: Aspergillus niger

<400> SEQUENCE: 6
caccgtgaaa gccatgctct ttccttcgtg tagaagacca gacag                     45

<210> SEQ ID NO 7
<211> LENGTH: 45
<212> TYPE: DNA
<213> ORGANISM: Aspergillus niger

<400> SEQUENCE: 7
ctggtcttct acacgaagga aagagcatgg ctttcacggt gtctg                     45

<210> SEQ ID NO 8
<211> LENGTH: 44
<212> TYPE: DNA
<213> ORGANISM: Aspergillus niger

<400> SEQUENCE: 8
ctatatacac aactggattt accatgggcc cgcggccgca gatc                      44

<210> SEQ ID NO 9
<211> LENGTH: 44
<212> TYPE: DNA
<213> ORGANISM: Aspergillus niger

<400> SEQUENCE: 9
gatctgcggc cgcgggccca tggtaaatcc agttgtgtat atag                      44

<210> SEQ ID NO 10
<211> LENGTH: 31
<212> TYPE: DNA
<213> ORGANISM: Aspergillus fumigatus

<400> SEQUENCE: 10
actggattta ccatgagatt cggttggctc g                                    31

<210> SEQ ID NO 11
<211> LENGTH: 31
<212> TYPE: DNA
<213> ORGANISM: Aspergillus fumigatus

<400> SEQUENCE: 11
agtcacctct agttactagt agacacgggg c                                    31

<210> SEQ ID NO 12
<211> LENGTH: 29
<212> TYPE: DNA
<213> ORGANISM: Trichoderma reesei

<400> SEQUENCE: 12
aacgttaatt aaggaatcgt tttgtgttt                                       29
```

```
<210> SEQ ID NO 13
<211> LENGTH: 29
<212> TYPE: DNA
<213> ORGANISM: Trichoderma reesei

<400> SEQUENCE: 13
agtactagta gctccgtggc gaaagcctg                                    29

<210> SEQ ID NO 14
<211> LENGTH: 26
<212> TYPE: DNA
<213> ORGANISM: Trichoderma reesei

<400> SEQUENCE: 14
actagtcgac cgaatgtagg attgtt                                       26

<210> SEQ ID NO 15
<211> LENGTH: 19
<212> TYPE: DNA
<213> ORGANISM: Trichoderma reesei

<400> SEQUENCE: 15
tgaccatggt gcgcagtcc                                               19

<210> SEQ ID NO 16
<211> LENGTH: 26
<212> TYPE: DNA
<213> ORGANISM: Trichoderma reesei

<400> SEQUENCE: 16
cgatcgtctc cctatgggtc attacc                                       26

<210> SEQ ID NO 17
<211> LENGTH: 28
<212> TYPE: DNA
<213> ORGANISM: Trichoderma reesei

<400> SEQUENCE: 17
actagttaat taagctccgt ggcgaaag                                     28

<210> SEQ ID NO 18
<211> LENGTH: 30
<212> TYPE: DNA
<213> ORGANISM: Aspergillus fumigatus

<400> SEQUENCE: 18
ggactgcgca ccatgagatt cggttggctc                                   30

<210> SEQ ID NO 19
<211> LENGTH: 30
<212> TYPE: DNA
<213> ORGANISM: Aspergillus fumigatus

<400> SEQUENCE: 19
tcgccacgga gcttactagt agacacgggg                                   30
```